(12) United States Patent
Beardsley et al.

(10) Patent No.: US 8,967,446 B2
(45) Date of Patent: Mar. 3, 2015

(54) VARIABLE COMPRESSION SURGICAL FASTENER CARTRIDGE

(75) Inventors: John Beardsley, Wallingford, CT (US); Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 1245 days.

(21) Appl. No.: 12/427,794

(22) Filed: Apr. 22, 2009

(65) Prior Publication Data

US 2009/0277948 A1    Nov. 12, 2009

Related U.S. Application Data

(60) Provisional application No. 61/051,923, filed on May 9, 2008.

(51) Int. Cl.
| | | |
|---|---|---|
| *A61B 17/04* | (2006.01) | |
| *A61B 17/10* | (2006.01) | |
| *A61B 17/072* | (2006.01) | |
| *A61B 17/064* | (2006.01) | |
| *A61B 17/115* | (2006.01) | |
| *A61B 17/00* | (2006.01) | |

(52) U.S. Cl.
CPC ....... *A61B 17/07207* (2013.01); *A61B 17/0644* (2013.01); *A61B 17/105* (2013.01); *A61B 17/1155* (2013.01); *A61B 2017/0023* (2013.01); *A61B 2017/07214* (2013.01); *A61B 2017/07228* (2013.01); *A61B 2017/07242* (2013.01); *A61B 2017/07271* (2013.01); *A61B 2017/07278* (2013.01)
USPC ....................................... 227/176.1

(58) Field of Classification Search
USPC .......... 227/176.1, 175.1–182.1; 606/142, 219
See application file for complete search history.

(56) References Cited

U.S. PATENT DOCUMENTS

| 1,756,670 A | 4/1930 | Treat |
| 3,258,012 A | 6/1966 | Nakayama et al. |
| 3,744,495 A | 7/1973 | Johnson |
| 3,771,526 A | 11/1973 | Rudie |

(Continued)

FOREIGN PATENT DOCUMENTS

| EP | 0129442 A1 | 12/1984 |
| EP | 169044 A2 | 1/1986 |

(Continued)

OTHER PUBLICATIONS

European Examination Report mailed Sep. 20, 2010 in European Patent Application No. EP 09 251 793.7.

(Continued)

*Primary Examiner* — Robert Long

(57) ABSTRACT

A non-reloadable surgical fastener cartridge is provided. The non-reloadable surgical fastener cartridge includes a cartridge body that includes a tissue contacting surface that includes a plurality of fastener retention slots. A plurality of surgical fasteners is disposed in the plurality of fastener retention slots. Each surgical fastener includes first and second legs of different lengths. A plurality of pushers is operably associated with the plurality of surgical fasteners. One or more of the pushers is configured such that, upon formation of a corresponding surgical fastener, a first area defined by the first leg is smaller than a second area defined by the second leg. The non-reloadable surgical fastener cartridge also includes an actuation mechanism operably associated with the plurality of pushers.

7 Claims, 12 Drawing Sheets

(56) References Cited

U.S. PATENT DOCUMENTS

| | | |
|---|---|---|
| 3,837,555 A | 9/1974 | Green |
| 4,014,492 A | 3/1977 | Rothfuss |
| 4,278,091 A | 7/1981 | Borzone |
| 4,319,576 A | 3/1982 | Rothfuss |
| 4,475,679 A | 10/1984 | Fleury, Jr. |
| 4,527,437 A | 7/1985 | Wells |
| 4,531,522 A | 7/1985 | Bedi et al. |
| 4,532,927 A | 8/1985 | Miksza, Jr. |
| 4,548,202 A | 10/1985 | Duncan |
| 4,573,469 A | 3/1986 | Golden et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,627,437 A | 12/1986 | Bedi et al. |
| 4,706,864 A * | 11/1987 | Jacobsen et al. ............ 227/109 |
| 4,741,336 A | 5/1988 | Failla et al. |
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,978,049 A | 12/1990 | Green |
| 4,979,954 A * | 12/1990 | Gwathmey et al. ........... 606/219 |
| 5,027,834 A | 7/1991 | Pruitt |
| 5,035,040 A * | 7/1991 | Kerrigan et al. .............. 29/505 |
| 5,108,422 A | 4/1992 | Green et al. |
| 5,180,092 A | 1/1993 | Crainich |
| 5,201,746 A | 4/1993 | Shichman |
| 5,209,756 A | 5/1993 | Seedhom et al. |
| 5,219,353 A | 6/1993 | Garvey, III et al. |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,352,229 A | 10/1994 | Goble et al. |
| 5,425,489 A | 6/1995 | Shichman et al. |
| 5,439,479 A | 8/1995 | Shichman et al. |
| 5,441,193 A | 8/1995 | Gravener |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,484,451 A * | 1/1996 | Akopov et al. ............... 606/139 |
| 5,497,931 A | 3/1996 | Nakamura |
| 5,501,693 A | 3/1996 | Gravener |
| 5,509,920 A | 4/1996 | Phillips et al. |
| 5,571,116 A | 11/1996 | Bolanos et al. |
| 5,571,285 A | 11/1996 | Chow et al. |
| 5,584,856 A | 12/1996 | Jameel et al. |
| 5,620,452 A | 4/1997 | Yoon |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,879,371 A | 3/1999 | Gardiner et al. |
| 5,911,353 A * | 6/1999 | Bolanos et al. ............ 227/180.1 |
| 5,915,616 A | 6/1999 | Viola et al. |
| 5,961,521 A | 10/1999 | Roger |
| 5,964,394 A | 10/1999 | Robertson |
| 6,083,242 A | 7/2000 | Cook |
| 6,202,914 B1 | 3/2001 | Geiste et al. |
| 6,273,897 B1 | 8/2001 | Dalessandro et al. |
| 6,325,810 B1 | 12/2001 | Hamilton et al. |
| 6,348,054 B1 | 2/2002 | Allen |
| 6,706,057 B1 | 3/2004 | Bidoia et al. |
| 6,786,382 B1 | 9/2004 | Hoffman |
| 6,877,647 B2 * | 4/2005 | Green et al. ............... 227/176.1 |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,001,411 B1 | 2/2006 | Dean |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,398,908 B2 | 7/2008 | Holsten et al. |
| 7,438,209 B1 * | 10/2008 | Hess et al. ................. 227/180.1 |
| 7,455,676 B2 | 11/2008 | Holsten et al. |
| 7,500,979 B2 | 3/2009 | Hueil et al. |
| 7,604,151 B2 * | 10/2009 | Hess et al. ................. 227/181.1 |
| 7,819,896 B2 * | 10/2010 | Racenet ....................... 606/219 |
| 2002/0042621 A1 | 4/2002 | Liddicoat et al. |
| 2004/0004105 A1 | 1/2004 | Jankowski |
| 2004/0073222 A1 | 4/2004 | Koseki |
| 2004/0093029 A1 | 5/2004 | Zubik et al. |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0023324 A1 | 2/2005 | Doll et al. |
| 2005/0023325 A1 | 2/2005 | Gresham et al. |
| 2005/0059996 A1 | 3/2005 | Bauman et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0085030 A1 | 4/2006 | Bettuchi et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola et al. |
| 2007/0010838 A1 | 1/2007 | Shelton, IV et al. |
| 2007/0075115 A1 | 4/2007 | Olson et al. |
| 2007/0095877 A1 | 5/2007 | Racenet et al. |
| 2007/0131732 A1 | 6/2007 | Holsten et al. |
| 2007/0262116 A1 | 11/2007 | Hueil et al. |
| 2008/0041918 A1 | 2/2008 | Holsten et al. |
| 2008/0078800 A1 | 4/2008 | Hess et al. |
| 2008/0078804 A1 | 4/2008 | Shelton et al. |
| 2008/0082124 A1 | 4/2008 | Hess et al. |
| 2008/0312687 A1 * | 12/2008 | Blier ........................... 606/219 |
| 2009/0255974 A1 * | 10/2009 | Viola ........................ 227/176.1 |

FOREIGN PATENT DOCUMENTS

| | | |
|---|---|---|
| EP | 0588081 A2 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1 607 048 A1 | 12/2005 |
| EP | 1728473 A1 | 12/2006 |

(56) References Cited

FOREIGN PATENT DOCUMENTS

| | | |
|---|---|---|
| EP | 1 754 445 A2 | 2/2007 |
| EP | 1 785 098 A2 | 5/2007 |
| EP | 1 875 868 A1 | 1/2008 |
| EP | 1917918 A2 | 5/2008 |
| EP | 2095777 A2 | 9/2009 |
| FR | 2838952 | 10/2003 |
| GB | 1 299 336 A | 12/1972 |
| GB | 2019296 A | 10/1979 |
| GB | 2029754 A | 3/1980 |
| GB | 2051287 A | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | 9619146 A1 | 6/1996 |
| WO | WO 97/34533 | 9/1997 |
| WO | 0230296 A2 | 4/2002 |
| WO | WO 03/094743 | 11/2003 |
| WO | WO 03/094747 | 11/2003 |
| WO | 2006/055385 A2 | 5/2006 |
| WO | 2008007377 A2 | 1/2008 |
| WO | WO 2008/003371 A1 | 1/2008 |
| WO | WO 2008/039249 A1 | 4/2008 |
| WO | WO 2008/039250 | 4/2008 |
| WO | 2008089050 A2 | 7/2008 |

OTHER PUBLICATIONS

European Search Report for EP 06016963.8-2318 date of completion is Mar. 9, 2007.
International Search Report from EP Application No. 07 25 4366 dated Nov. 11, 2010.
International Search Report from EP Application No. 09 25 1067 mailed Mar. 17, 2011.
European Search Report dated Jan. 31, 2011 for European Patent Appln. No. EP 10 25 1797.
European Search Report for EP 09251276.3-2310 date of completion is Apr. 13, 2012 (8 pages).
European Search Report ESR 08252283.0-1526.
European Search Report ESR 09251224.3-2310.
European Search Report ESR 09251268.0-2310.
European Search Report ESR 11004299.1269.
European Search Report ESR 9251240.9.

\* cited by examiner

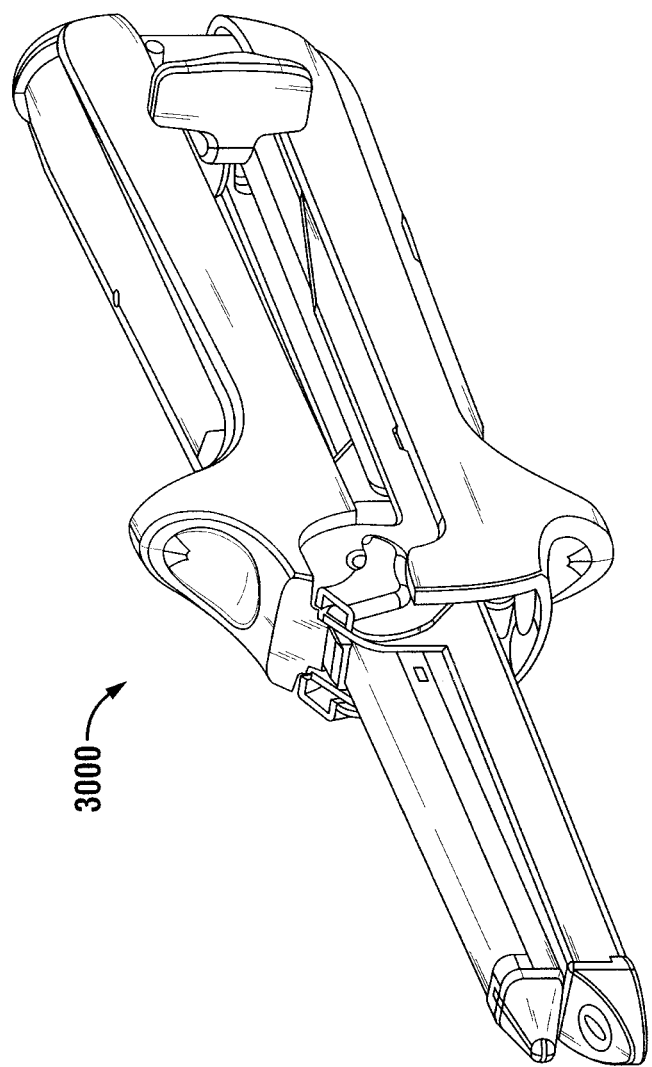

VARIABLE COMPRESSION SURGICAL FASTENER CARTRIDGE

CROSS-REFERENCE TO RELATED APPLICATIONS

This application claims priority to U.S. Provisional Application Ser. No. 61/051,923 filed May 9, 2008, the contents of which is incorporated herein by reference in its entirety.

BACKGROUND

1. Technical Field

The present disclosure relates to surgical fastener applying apparatus. More particularly, the present disclosure relates to a surgical fastener cartridge that includes a plurality of surgical fasteners configured so as to have areas of different sizes, depending on the location of the tissue with respect to the cartridge, and potentially to apply different compressive forces to tissue, and methods of manufacturing and using the same.

2. Background of the Related Art

Commercially available surgical fastening apparatus are well known in the art, some of which are specifically adapted for use in various surgical procedures including, but not limited to, anastomosis. U.S. Pat. Nos. 5,915,616; 6,202,914; 5,865,361; and 5,964,394 each describe one or more suitable apparatus which may be employed while performing one of these procedures.

In general, a surgical fastening apparatus will include an anvil that is approximated relative to a fastener cartridge during use. The anvil includes depressions that are aligned with, and/or are in registration with slots defined in the cartridge, through which the fasteners will emerge. To effectuate formation, the fasteners emerge from the cartridge and are driven against the anvil. The fastener cartridge typically has one or more rows of fasteners disposed alongside a longitudinal slot that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners have a pre-formed configuration and a formed configuration. Unitary fasteners generally include a pair of legs adapted to penetrate tissue and connected by a backspan from which they extend. In use, subsequent to formation, certain types of unitary fasteners have a "B" shaped configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. They are generally made of a bioabsorbable material.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing. It may also be desirable to cut and staple across tissue that varies in thickness. It would therefore be advantageous to provide staples which could better accommodate these resulting different tissue thicknesses.

SUMMARY

The present disclosure provides a surgical fastener cartridge. The surgical fastener cartridge includes a cartridge body that includes a tissue contacting surface. The tissue contacting surface includes a plurality of fastener retention slots. In embodiments, each of the plurality of fastener retention slots are angled forming inner and outer ends with respect to the slot. The cartridge body includes a plurality of surgical fasteners disposed in the plurality of fastener retention slots; each of the surgical fasteners having a first leg and a second leg. In embodiments, the first leg of the surgical fastener includes a length that is shorter than a length of the second leg of the surgical fasteners. In embodiments, the first and second legs of the surgical fastener are connected by a backspan that defines an angle with respect to the tissue contacting surface. The cartridge body includes a plurality of pushers operably associated with the plurality of surgical fasteners; each pusher configured for ejecting an associated surgical fastener towards a depression in an anvil. One or more of the pushers may be configured such that, upon formation of a corresponding surgical fastener, a first area defined by the first leg is smaller than a second area defined by the second leg. In embodiments, each of the formed surgical fasteners includes a first loop defining the first area and a second loop defining the second area. In embodiments, one or more of the surgical fasteners includes a recess in the backspan thereof, prior to formation. An actuation mechanism may be operably associated with the plurality of pushers.

In embodiments, the tissue contacting surface includes a slot configured to accommodate longitudinal movement of a cutting element.

In embodiments, the surgical fastener has portions with different diameters.

In embodiments, a top surface of the one or more pushers is sloped.

In embodiments, the backspan of the surgical fastener follows substantially the same contour as the top surface the at least one pusher.

The present disclosure also provides surgical fastener cartridge that includes a cartridge body that includes a tissue contacting surface. The tissue contacting surface includes a plurality of fastener retention slots and a knife slot configured to accommodate longitudinal movement of a cutting element. In embodiments, each of the plurality of fastener retention slots may be angled forming inner and outer ends with respect to the knife slot. The cartridge body includes a plurality of surgical fasteners that are disposed in the plurality of fastener retention slots; each surgical fastener having a first end that is closer to the knife slot than a second end. In embodiments, the surgical fastener includes a first leg at the first end and a second leg at the second end. The first leg may include a length that is shorter than a length of the second leg. In embodiments, the first and second leg of each of the surgical fasteners is connected by a backspan that defines an angle with respect to the tissue contacting surface. In embodiments, one or more of the surgical fasteners may include a recess in the backspan thereof, prior to formation. The cartridge body includes a plurality of pushers operably associated with the plurality of surgical fasteners; each pusher configured to eject an associated surgical fastener towards a depression in an anvil. One or more of the pushers includes a corresponding surgical fastener and the one or more pushers may be configured such that, upon formation, the first end of the corresponding surgical fastener is smaller in height than the second end of the corresponding surgical fastener. In embodiments, each of the formed surgical fasteners includes a first loop and a second loop. An actuation mechanism may be operably associated with the plurality of pushers.

In embodiments, the surgical fastener has portions with different diameters.

In embodiments, a top surface of the one or more pushers is sloped.

In embodiments, the backspan of the surgical fastener follows substantially the same contour as the top surface the at least one pusher.

The present disclosure additionally provides a surgical fastener applying apparatus. The surgical fastener applying apparatus includes a handle assembly, an elongated shaft extending distally from the handle assembly; and an operative tool adapted to couple to the shaft. The operative tool includes a pair of opposed jaws pivotally coupled to one another and respectively including an anvil member and a non-reloadable surgical fastener cartridge that are approximated relative to one another during use. In certain embodiments, the non-reloadable surgical fastener cartridge includes a cartridge body that includes a tissue contacting surface. The tissue contacting surface includes a plurality of fastener retention slots. In embodiments, each of the plurality of fastener retention slots are angled forming inner and outer ends with respect to the slot. The cartridge body includes a plurality of surgical fasteners disposed in the plurality of fastener retention slots; each of the surgical fasteners having a first leg and a second leg. In embodiments, the first leg of the surgical fastener includes a length that is shorter than a length of the second leg of the surgical fasteners. In embodiments, the first and second legs of the surgical fastener are connected by a backspan that defines an angle with respect to the tissue contacting surface. The cartridge body includes a plurality of pushers operably associated with the plurality of surgical fasteners; each pusher configured for ejecting an associated surgical fastener towards a depression in an anvil. One or more of the pushers may be configured such that, upon formation of a corresponding surgical fastener, a first area defined by the first leg is smaller than a second area defined by the second leg. In embodiments, each of the formed surgical fasteners includes a first loop defining the first area and a second loop defining the second area. In embodiments, one or more of the surgical fasteners includes a recess in the backspan thereof, prior to formation. An actuation mechanism may be operably associated with the plurality of pushers.

In embodiments, the tissue contacting surface includes a slot configured to accommodate longitudinal movement of a cutting element.

In embodiments, the surgical fastener has portions with different diameters.

In embodiments, a top surface of the one or more pushers is sloped.

In embodiments, the backspan of the surgical fastener follows substantially the same contour as the top surface the at least one pusher.

BRIEF DESCRIPTION OF THE DRAWINGS

Various embodiments of the present disclosure are described hereinbelow with references to the drawings, wherein:

FIG. 3 illustrates another type of surgical fastener instrument that employs an alternate embodiment of surgical fastener cartridge in accordance with the present disclosure;

DETAILED DESCRIPTION OF EMBODIMENTS

Figure 1:
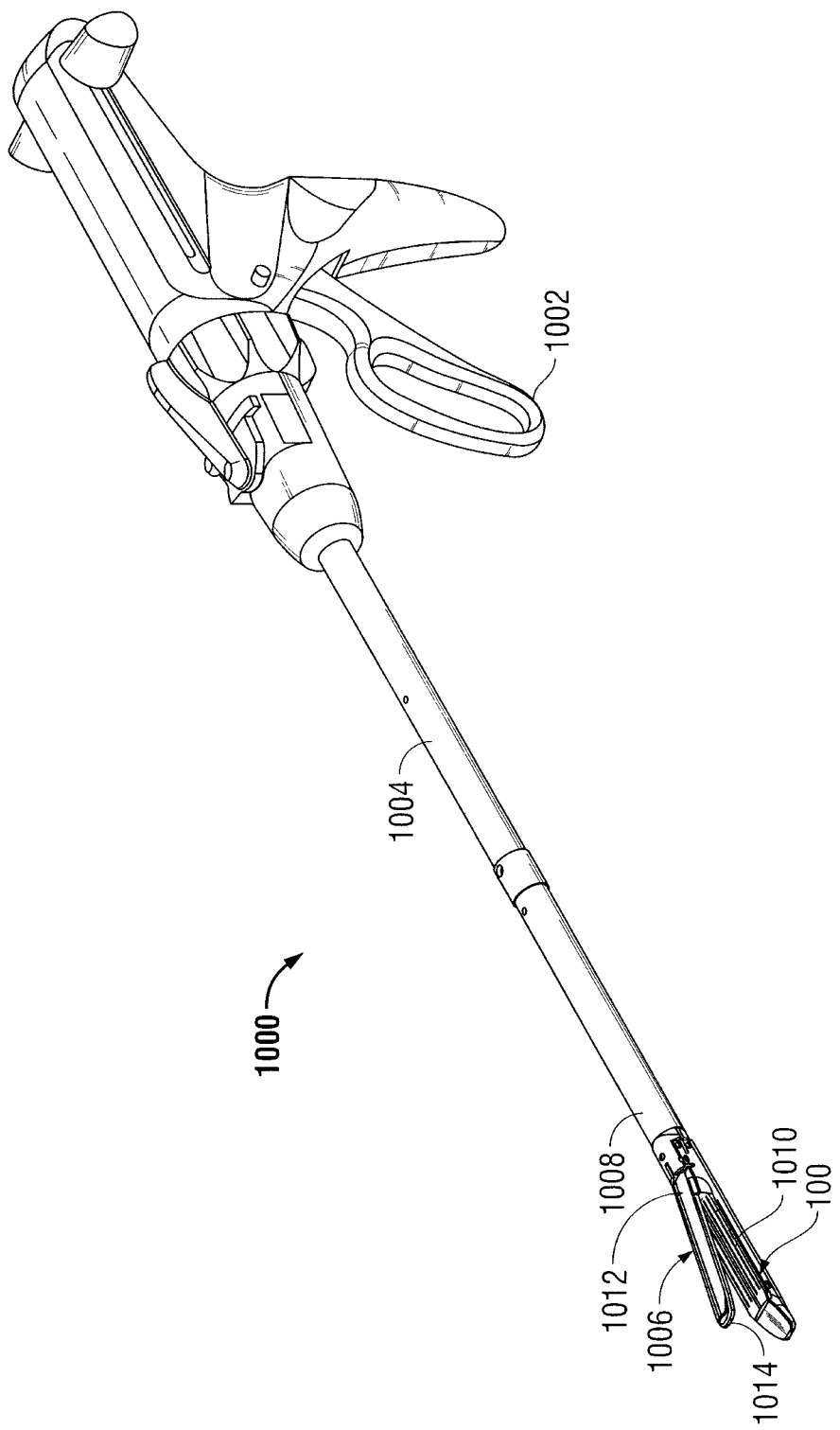
FIG. 1 illustrates a surgical fastener applying apparatus for use with a surgical fastener cartridge that employs surgical fasteners in accordance with an embodiment of the present disclosure.

Various embodiments of the presently disclosed surgical fastener cartridge will now be described in detail with reference to the drawings wherein like reference numerals identify similar or identical elements. In the drawings and in the description which follows, the term "proximal" will refer to the end of the surgical fastener cartridge that is closer to the operator during use, while the term "distal" will refer to the end of the fastener cartridge that is farther from the operator, as is traditional and conventional in the art. In addition, the term "surgical fastener" should be understood to include any structure formed of a biocompatible material that is suitable for the intended purpose of joining tissue together, including but not being limited to surgical staples, clips, and the like.

The present disclosure provides a surgical fastener cartridge adapted to house a plurality of surgical fasteners configured so as to have areas of different sizes, depending on the location of the tissue with respect to the cartridge, and potentially to apply different compressive forces to tissue, such that a hemostatic effect may be achieved. To this end, certain embodiments have surgical fasteners each of which includes two legs each configured to provide a different compression force to stapled tissue when formed.

With reference to FIG. 1, a surgical fastener applying apparatus 1000 that employs a surgical fastener cartridge 100 is illustrated. Surgical fastener applying apparatus 1000 is used to sequentially apply a plurality of surgical fasteners to a patient's tissue. Surgical fastener apparatus 1000 may be configured for use, subsequent sterilization and reuse, or may be configured for single use. Surgical fastener applying apparatus 1000 includes a handle or trigger 1002, an elongated shaft 1004 extending distally therefrom, and an operative tool 1006 coupled to a distal end 1008 of the elongated shaft 1004. In general, operative tool 1006 is adapted to clamp, sequentially fasten together, and sever adjacent tissue segments along a cut-line, or longitudinal slot 122. Operative tool 1006 includes a pair of opposed jaws 1012, 1010 pivotally coupled to one another and respectively including an anvil member 1014 and cartridge 100 that are approximated relative to one another during use. The anvil 1014 includes an anvil plate 90 having depressions 91 (see FIG. 5A) that are aligned with, and/or are in registration with fastener retention slots 126 (FIG. 4A) defined in the cartridge 100, through which the fasteners 130 will emerge, to be driven against anvil plate 90 (see FIGS. 5A and 5B). For a more detailed discussion of the approximation and firing of surgical fastener applying apparatus 1000, reference is made to commonly owned U.S. Pat. Nos. 7,258,262 and 5,865,361 currently assigned to Tyco Healthcare Group LP, the entire contents of which are hereby incorporated herein by reference. The operative tool 1006 and/or cartridge 100 may be a removable and/or replaceable loading unit for the apparatus 1000.

Figure 2:
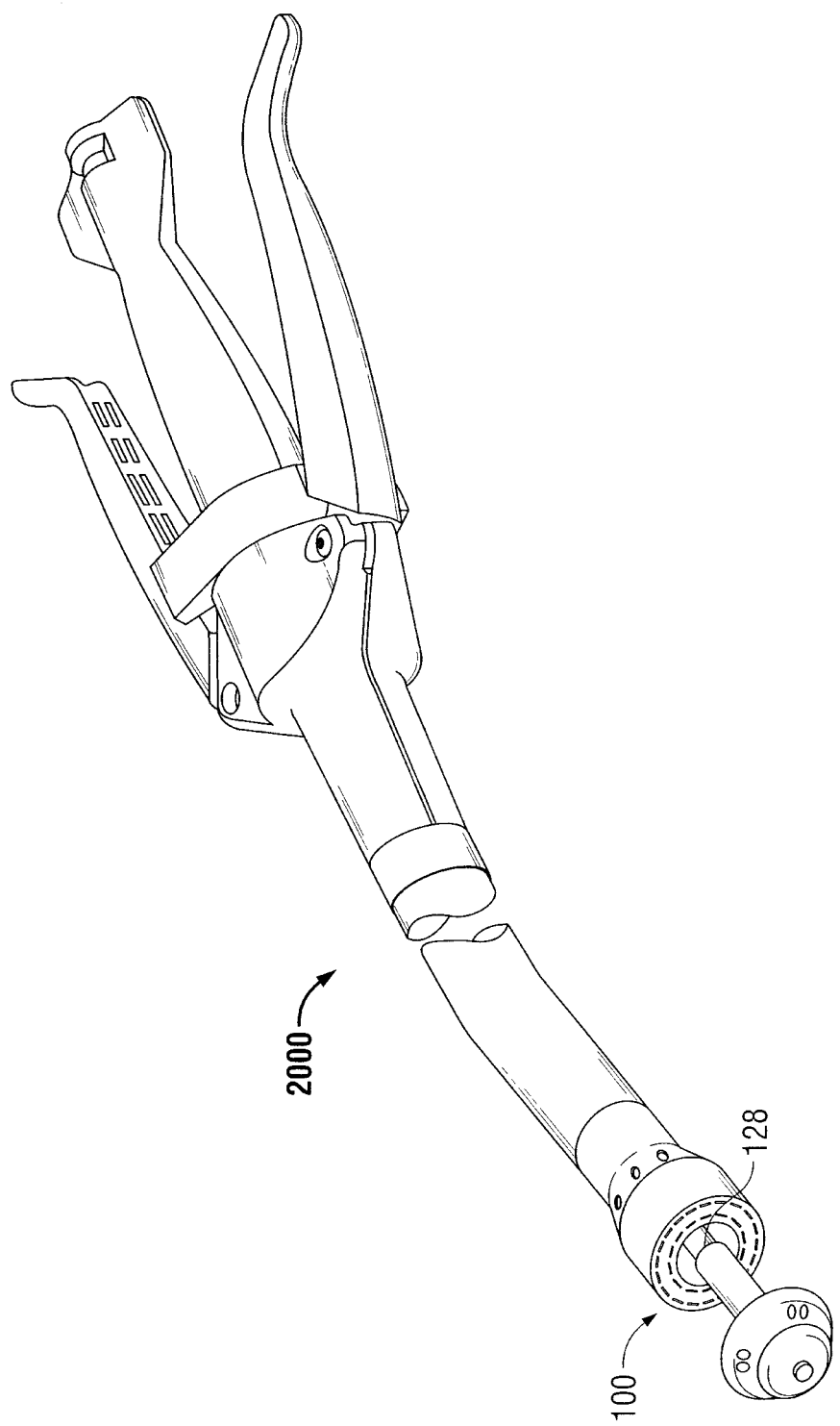
FIG. 2 illustrates another type of surgical fastener device that employs an alternate embodiment of a surgical fastener cartridge in accordance with the present disclosure.

While surgical fastener applying apparatus 1000 is depicted as an apparatus suitable for use in laparoscopic procedures for performing surgical anastomotic fastening of tissue, those skilled in the art will appreciate that cartridge 100 may be adapted for use with any surgical fastening instrument. For example, cartridge 100 may be adapted for use with an end-to-end anastomosis device 2000, as seen in FIG. 2, and/or a surgical stapling instrument 3000, as seen in FIG. 3, for use during an open gastrointestinal anastomotic stapling procedure, or, for example, any of the surgical fastener applying apparatus discussed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each hereby incorporated by reference herein in their entirety. The cartridge in certain embodiments is removable and replaceable with another loaded cartridge. In other embodiments, the operative tool 1006 is removable and replaceable.

For the purposes of brevity, the structural and operational features of cartridge 100 will be described in terms of use with the surgical fastener applying apparatus 1000.

Figure 4A:
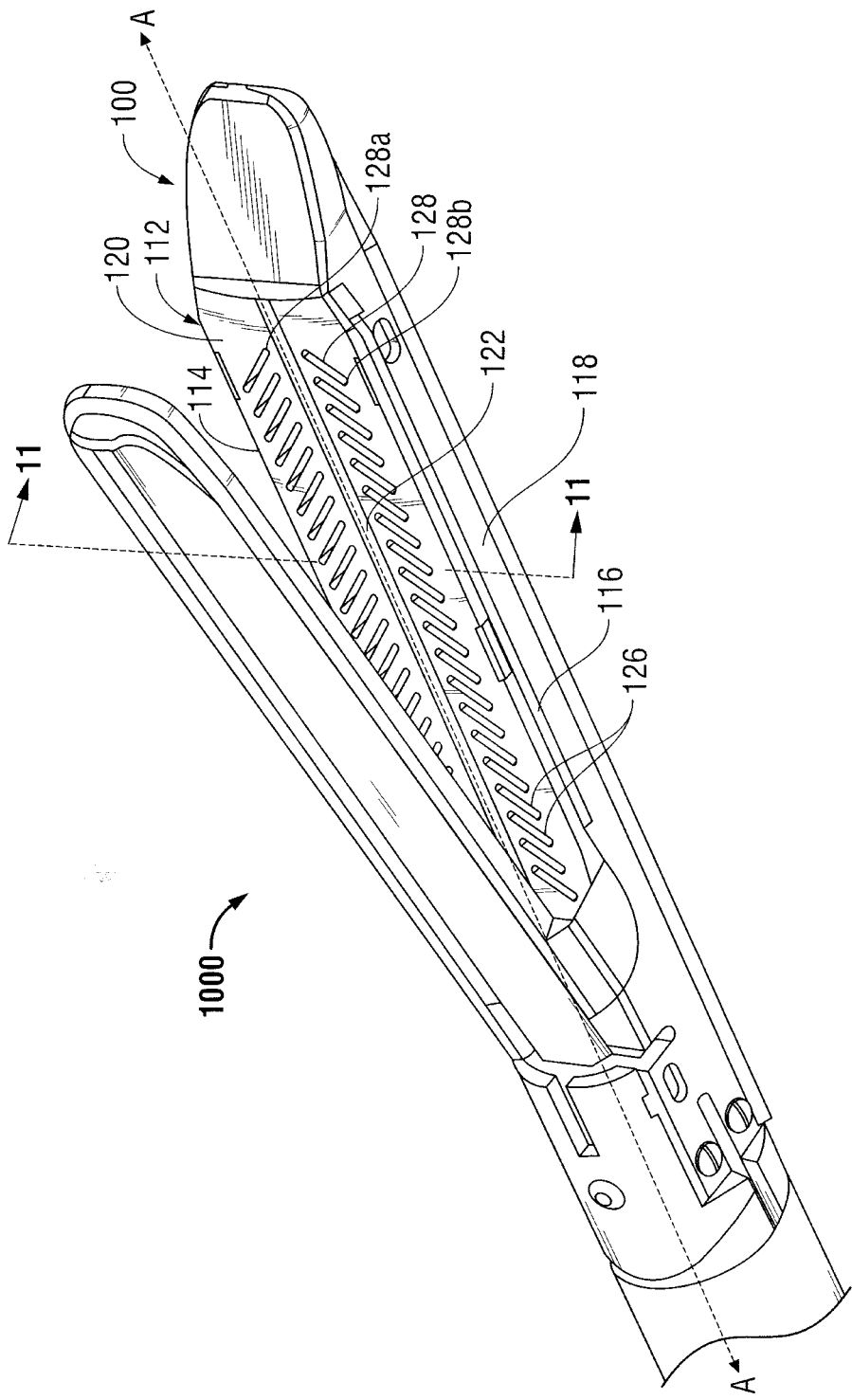
FIG. 4A is an enlarged top perspective view of the surgical fastener cartridge configured for use with the surgical fastener applying apparatus shown in FIG. 1.
Figure 4B:
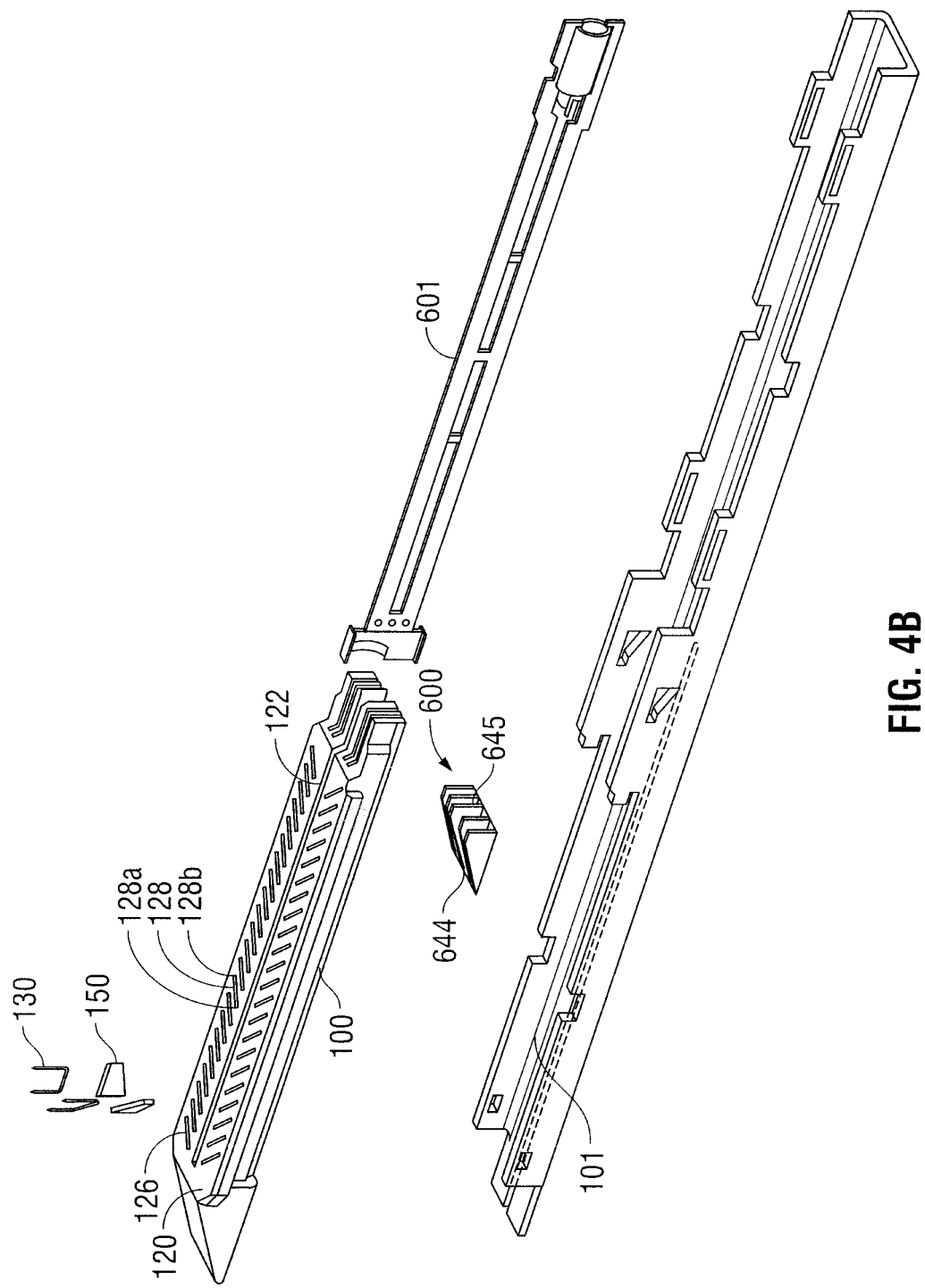
FIG. 4B is a partially exploded view of an alternate embodiment of a surgical fastener loading unit configured for use with the surgical fastener applying apparatus depicted in FIG. 3.
Figure 5A:
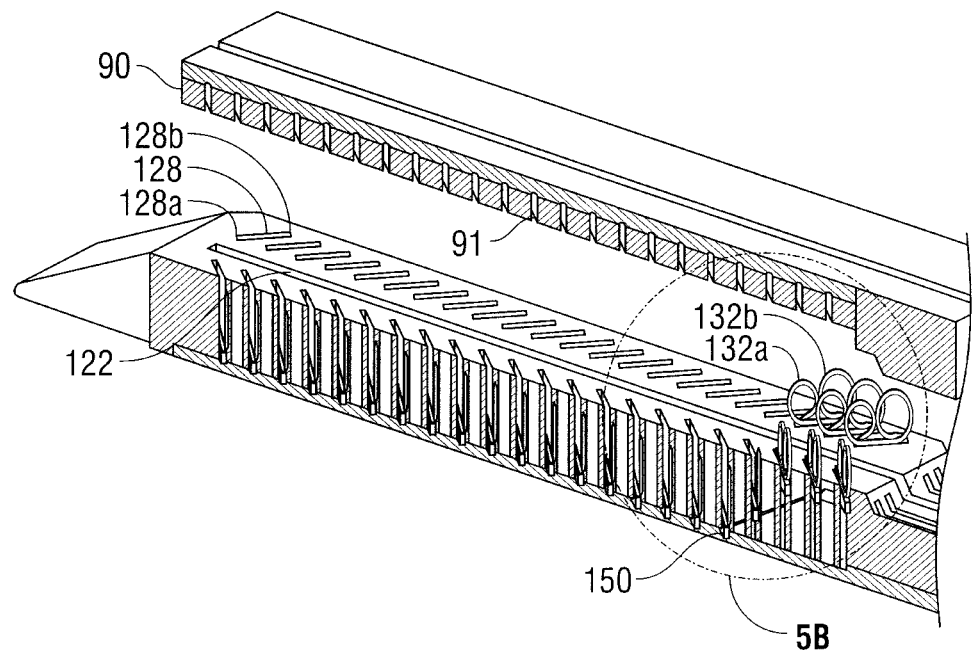
FIG. 5A is a partial cross-sectional view of the surgical fastener cartridge depicted in FIG. 4B with the surgical fastener shown subsequent to formation.

With reference to FIGS. 4A and 4B, and initially with reference to FIG. 4A cartridge 100 is shown. Cartridge 100 extends along a longitudinal axis "A-A" and includes a cartridge body 112 with a pair of opposed side walls 114, 116, a bottom wall 118, and a tissue contacting surface 120. The tissue contacting surface 120 includes a longitudinal slot 122 that is configured to accommodate longitudinal movement of a knife bar 601, or other suitable cutting element, such that stapled tissue may be severed along a cut-line. The tissue contacting surface 120 includes a plurality of fastener retention slots 126 arranged into a plurality of rows 128 that extend substantially the length of the cartridge 100. As shown in FIG. 4A, the fastener retention slots 126 are arranged into rows 128 that are spaced laterally from the longitudinal slot 122. Retention slots 126 are configured such that deployment of the surgical fastener 130 and subsequent formation thereof, provides a formed surgical fastener with an end that is closer to the cut-line and an end that is farther from the cut-line, or longitudinal slot 122. To this end, retention slots 126 are angled with respect to longitudinal slot 122, as best seen in FIG. 4A, such that inner (closest to the longitudinal slot) and outer ends (farthest to the longitudinal slot) $128_A$ and $128_B$, respectively, are formed. While the cartridge 100 is depicted as including pairs of rows 128, it is within the purview of the present disclosure to have more or fewer rows of the fastener retention slots 126 disposed on cartridge 100. Additionally, rows 128 may be annular, as opposed to linear, and spaced radially from the cutting element; such is the case when the fastening cartridge is employed with the surgical fastening device depicted in FIG. 2. In addition, the retention slots 126 could be aligned with a longitudinal axis of the fastening cartridge.

Figure 11:
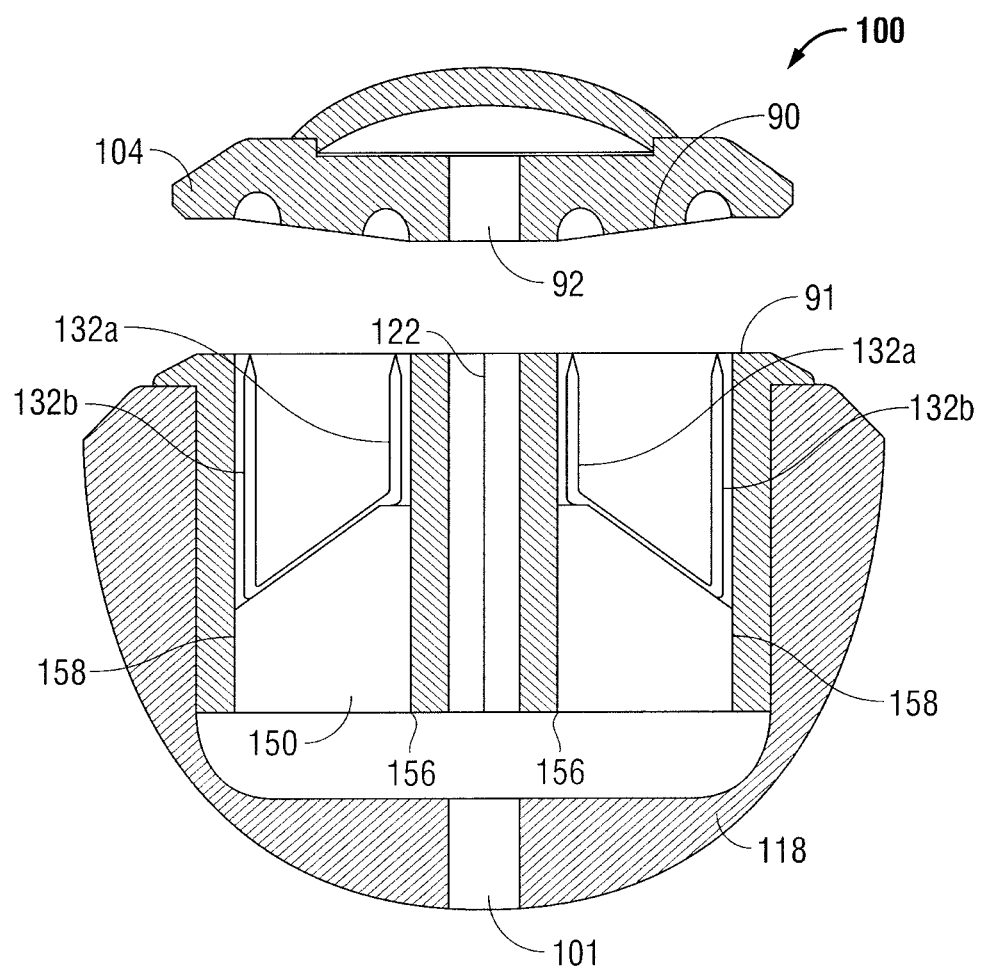
FIG. 11 is partial cross-sectional view taken along the line segment "11-11" of FIG. 4A illustrating the surgical fastener cartridge loaded with the surgical fasteners depicted in FIG. 6.

With reference to FIG. 4B, each of the fastener retention slots 126 is configured to receive one of a plurality of surgical fasteners 130 therein such that the surgical fasteners 130 are deployed in rows on opposite sides of the cut-line, or longitudinal slot 122 created in the tissue during fastening, see FIG. 11 for example. Pushers 150 are operatively associated and aligned with fastener retention slots 126 and are sequentially contacted by one or more cam wedges 644 (four cam wedges are shown) of an actuation sled 600 as actuation sled 600 is driven distally through cartridge 100 by an axial drive assembly which includes knife bar 601 and an abutment surface which engages the central support wedge 645 of actuation sled 600. Axial drive assembly, among other things, transmits the longitudinal drive forces exerted by a control rod (not shown) disposed in elongated shaft 1004 to the actuation sled 600 disposed such that the actuation sled 600 engages the respective pushers 150. Pushers 150 interact with the plurality of surgical fasteners 130 housed within staple cartridge 100 to sequentially eject the surgical fasteners 130 therefrom (FIG. 4B). An example of a drive assembly is disclosed in commonly owned U.S. Pat. No. 7,258,262, the contents of which are hereby incorporated by reference in its entirety.

In order to move the anvil member between the open and closed positions, surgical stapling instrument 1000 includes a trigger or handle 1002 pivotally mounted to the handle assembly. Handle 1002 controls the linear movement of a control rod (not shown) which is mounted within the elongated tubular member 1004. The control rod operates to move the knife bar 601 distally to initially move the anvil member and/or slot 101 between the open and closed positions. The knife bar also acts to move the sled (not shown) distally through the staple cartridge 18 to eject staples. The knife bar desirably includes a knife blade to cut tissue as the knife bar translates through the staple cartridge 18, but the knife bar may be configured as a series of cam bars and a separate knife.

Although surgical stapling instrument 12 is shown with a single movable handle 1002 which accomplishes both jaw closure and firing of staples, it is further contemplated that the present buttress release mechanism can also be used with surgical stapling instruments of the type which utilize a clamping mechanism to close the jaws which is separate from the firing mechanism. See, for example, U.S. Pat. No. 5,476,206, the contents of which are expressly incorporated herein by reference.

Figure 5B:
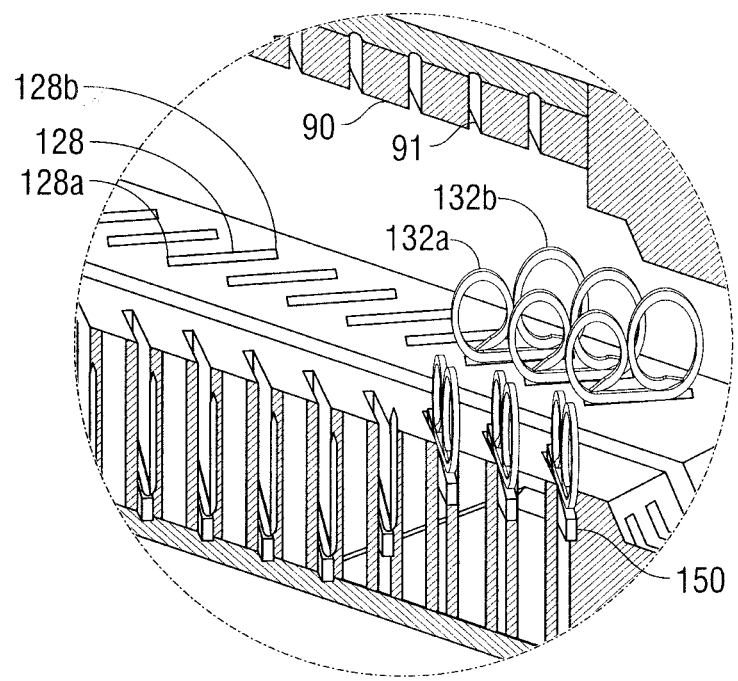
FIG. 5B is an enlarged view of the area of detail represented by 5B depicted in FIG. 5A.

In operation, prior to firing stapling apparatus 1000, actuation sled 600 is in a proximal-most position. At such a time, knife bar 601 is disposed adjacent a proximal end of cartridge 100 and proximal to the sled 600. The knife bar 601 of the axial drive assembly has an upper member that engages a slot 92 disposed within the anvil member 90 and a lower member that engages the slot 101 that supports the cartridge 100 (see FIG. 11). The operative tool 1006 is first actuated to clamp onto tissue. Movable handle 1002 of the handle assembly advances the control rod distally. The control rod advances the knife bar so that the upper and lower members of the knife bar engage the anvil member 90 and slot 101 respectively to approximate the anvil member 90 and cartridge 100 with one another. With tissue clamped between anvil member 90 and cartridge 100, the fasteners are fired from the apparatus into the tissue. The handle 1002 is again operated to further advance the knife bar. Accordingly, a drive bar drives actuation sled 600 distally through cartridge 100. During its distal translation, the angled leading surfaces of cam wedges 644 sequentially contact pushers 150, urging them in a direction perpendicular to the direction of movement of actuation sled 600 (FIG. 5A), toward the anvil. As a result, pushers 150 push surgical fasteners 130 from their individual slots, driving each surgical fastener 150 into a respective forming depression 91 of anvil plate 90 (FIG. 5B). The forming depressions are configured to form the surgical fasteners into the desired shape. Sequential firing of the staples continues until actuation sled 600 is advanced to the distal end of cartridge 100, at which time, all of the staples once housed within cartridge 100 will have been ejected. A more detailed description of the interaction between actuation sled 600 and pushers 150 will be described below.

With reference now to FIGS. 6 and 7A-7D, cartridge 100 may loaded with one or more varieties of surgical fastener, represented generally as surgical fastener 130. Surgical fastener 130 includes two legs 132, a first leg 132$_A$ and a second leg 132$_B$ each having different lengths and connected by a backspan 134 extending therebetween. In the embodiment shown, backspan 134 is at an angle with respect to both of legs 132 and follows substantially the same contour as a top surface 152 of pusher 150, see FIG. 10 for example. Backspan 134 may be slanted at any angle with respect to each of legs 132$_A$, 132$_B$ and top surface 152 of pusher 150. The thickness of the backspan 134 and the legs 132 may be varied to fasten adjacent tissue segments "T$_1$", "T$_2$" of varying thickness (see FIG. 8). In certain embodiments, the backspan of the surgical fastener has a recess defined therein, prior to formation. The recess generally reduces the interior space or area of the formed surgical fastener, see FIG. 7E for example.

The legs 132 and the backspan 134 may define a cross-section having any suitable geometric configuration, including but not limited to rectangular, oval, square, triangular, and trapezoidal. The legs 132 and the backspan 134 may exhibit the same geometrical configuration such that the cross-sectional configuration of the surgical fastener 130 is substantially uniform, or, alternatively, the legs 132 and the backspan 134 may exhibit different geometrical configurations, e.g., the legs 132 may exhibit a rectangular cross-section and the backspan 34 may exhibit an oval cross-section, as shown in FIGS. 7A-7D. Backspan 134 and/or legs 132 may be formed by any suitable means known in the art including but not limited to welding, braising, coining, casting, overmolding and so on. Additionally, backspan 134 and/or legs 132 may be treated by way of annealing, cold working, heat treating, and so on. This may provide increased burst strength to the surgical fastener. Moreover, backspan may include different configurations of blocking and/or retainer material, tube, sleeve, collar, and/or grommet.

Figure 6:
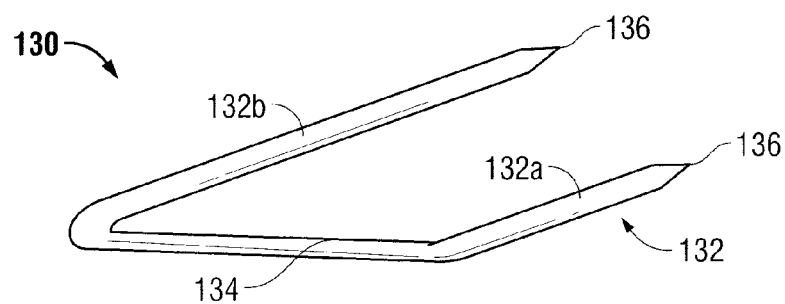
FIG. 6 is a side perspective view of a surgical fastener configured for use with the cartridge depicted in FIG. 4A prior to formation.

As seen in FIG. 6, prior to the formation of surgical fastener 130, legs 132 extend from the backspan 134 such that they are substantially parallel. Alternatively, the legs 132 may converge or diverge from the backspan. The present disclosure contemplates that the surgical fastener 130 may also be configured as a directionally biased staple, such as those described in commonly owned U.S. patent application Ser. No. 11/253,493, filed Oct. 17, 2005, the entire contents of which are incorporated by reference herein.

Each of the legs 132 terminates in a penetrating end 136 that is configured to penetrate tissue (tissue segments "T$_1$", "T$_2$" for example) and/or other suitable material (blocking and/or retainer material for example). The penetrating ends 136 of legs 132 can be tapered to facilitate the penetration of tissue segments "T$_1$", "T$_2$", or alternatively, the penetrating ends 136 may not include a taper. In various embodiments, penetrating ends 136 may define a conical or flat surface, as described in co-pending U.S. patent application Ser. No. 11/444,761, filed Apr. 13, 2003, the entire contents of which are incorporated by reference herein. In embodiments, one or both of legs 132 may be barbed. Having legs 132 configured in such a manner may facilitate maintaining the surgical fastener 130 in a fixed position within the tissue and/or blocking material. In certain embodiments, each of legs 132 has different lengths. More particularly, the leg 132 closer to the cut-line, or longitudinal slot 122 (e.g., leg 132$_A$) will have a shorter length than the leg 132 farther from the cut-line, or longitudinal slot 122 (e.g., leg 132$_B$). A more detailed description of the legs 132 will be described below.

Figure 8:
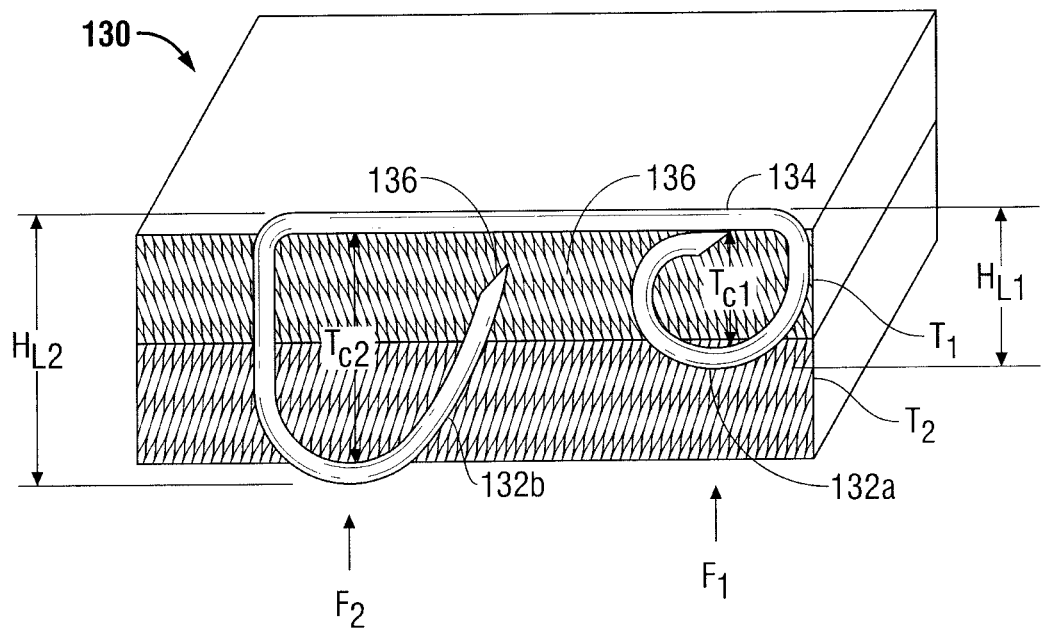
FIG. 8 is a side cross-sectional view of the surgical fastener depicted in FIG. 6 shown subsequent to formation and within adjacent tissue segments.

Turning now to FIG. 8, surgical fastener 130 is shown subsequent to formation. Surgical fastener 130 is configured to provide a compression force to stapled tissue occupied therein. To this end, legs 132$_A$ and 132$_B$ cooperate with backspan 134 to maintain adjacent tissue segments or layers "T$_1$", "T$_2$" in approximation and apply respective compressive forces "F$_1$" and "F$_2$" thereto. The respective compressive forces "F$_1$" and "F$_2$" applies pressure to the tissue segments "T$_1$", "T$_2$", thereby restricting the flow of blood through the tissue surrounding the surgical fastener 130 and facilitating hemostasis. The amount of pressure that is applied to the tissue segments "T$_1$", "T$_2$" is limited such that the flow of blood through the tissue is not completely restricted. When formed, surgical fastener 130 is generally "B" shaped having a first loop at a first end of the surgical fastener with an overall height "H$_{L1}$" and a respective tissue compression space or area Tc$_1$, and a second loop at a second end of the surgical fastener with an overall height "H$_{L2}$" and a respective tissue compression space Tc$_2$ (each tissue compression space or area measured from the outermost surface of the backspan 134 to the outermost curve of the legs 132).

Figure 9:
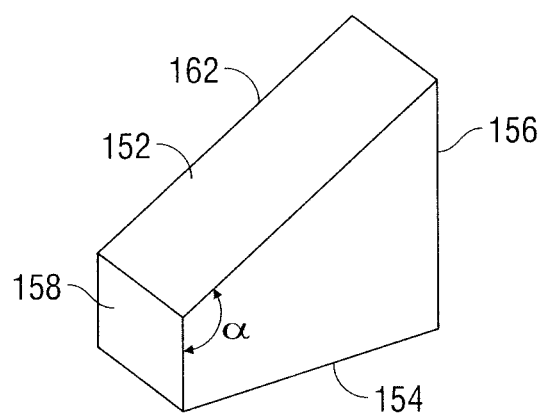
FIG. 9 is a side perspective view of a pusher configuration depicted in FIG. 4B.
Figure 10:
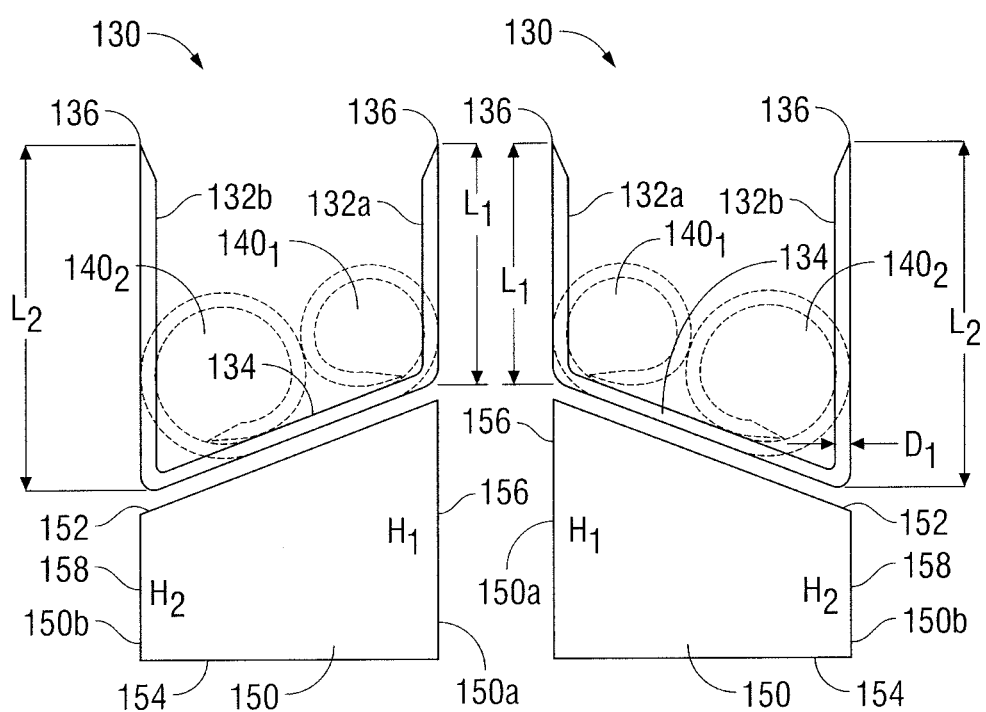
FIG. 10 illustrates the surgical fastener depicted in FIG. 6 being shown prior to and subsequent to formation (in phantom)

With reference to FIGS. 9 and 10, an initially with reference to FIG. 9, pusher 150 is shown. As noted above, cartridge 100 is configured such that the leg 132 of the surgical fastener 130 deployed closer to the cut-line or slot 122 provides a greater compression force to the stapled tissue than the leg 132 of the surgical fastener 130 deployed farther from the cut line, longitudinal slot 122. To this end, pusher 150 is configured such that a portion 150*a* of the pusher 150 driving the leg 132 of the surgical fasteners 130 closer to the cut-line or longitudinal slot 122 has greater height than a portion 150*b* of the pusher 150 driving the leg 132 of the surgical fasteners farther from the cut-line or slot 122 (see FIG. 10, for example).

Pusher 150 includes a base 154 and two sidewalls 156, 158 extending in a generally orthogonal direction therefrom. Pusher 150 may include structure similar to conventional pushers known in the art. While base 154 is shown having a generally linear configuration, it is within the purview of the present disclosure for base 154, or portion thereof, to be curved or angled. Having base 154 curved or angled may facilitate operative interaction between sled 600 and pusher 150. Base 154 of pusher 150 may have any suitable width "W". Sidewall 156 supports corresponding leg portion $132_A$ and has a height "$H_1$", while sidewall 158 supports corresponding leg portion $132_B$ and has a height "$H_2$ (see FIG. 10). Height "$H_1$" of sidewall 156 being greater than height "$H_2$" of sidewall 158. As noted above, pusher 150 includes a top surface 152. Top surface 152 is oblique or slanted and extends from sidewall 156 to sidewall 158. Having pusher 150 configured in such a manner facilitates forming of surgical fastener 130 against depressions 91 of anvil plate 90. Top surface 154 may extend from the sidewalls 156, 158 at any suitable angle "α" (FIG. 9). More particularly, angle "α" may be equal to, less than, and/or greater than the angle or slant that backspan 134 extends with respect to each of legs $132_A$, $132_B$. Pusher 150 also includes front and rear walls 160, 162, respectively. In further embodiments, the top surface 152 may be stepped, with two or more generally horizontal surfaces.

Those skilled in the art will appreciate that several variations of the above described pusher configurations may be employed to achieve the same or similar result. For example, instead of having sidewalls 156, 158 with different heights, sidewalls 156, 158, may have similar heights and include any number of intents, detents, slits, slots, or other suitable structure configured to raise or lower a corresponding leg of a surgical fastener. Part of the pusher may comprise a collapsible or compressible material to correspond to a portion of a fastener having a larger compressive space.

As noted, in certain embodiments, the legs 132 supported by sidewalls 156 (e.g., legs $132_A$), and thus closest to the cut-line or longitudinal slot 122, are shorter and as a result are intended to form a smaller loop. In operation, when cam wedges 644 contact and drive pushers 150, the corresponding legs $132_A$ of surgical fasteners 130 forms a loop, or other generally closed shape, when it is urged against the anvil plate 90, thereby restricting the flow of blood through the tissue surrounding the surgical fastener 130 and facilitating hemostasis. As also noted, the legs supported by sidewalls 158 (e.g., legs $132_B$), and thus farther from the cut-line, are longer and as a result are intended to form a larger loop, or generally closed shape. In operation, when cam wedges 644 contact and drive pushers 150, the corresponding legs $132_B$ of surgical fasteners 130 forms a larger loop when the surgical fastener 130 is urged against the anvil plate 90, thereby allowing some blood to flow through the tissue surrounding the surgical fastener 130 and facilitating healing, as best seen in FIG. 5B.

With reference again to FIG. 10 formation of surgical fastener 130 will be described. In the following description, cam wedges 644 of sled 600 are configured to provide the driving force for pushers 150 and surgical fasteners 130. As shown, surgical fastener 130 has a diameter "$D_1$" and includes legs $132_A$ and $132_B$ that have respective lengths "$L_1$" and "$L_2$". Legs $132_A$ and $132_B$ are substantially similar to each other. The overall heights of the legs $132_A$, $132_B$ in the unformed condition (measured from the penetrating tip 136 of the legs to the outermost surface of the backspan 134) are shown with leg $132_A$ being shorter than leg $132_B$. Surgical fasteners $130_A$ are shown in their initial and formed conditions (in phantom). The backspan 134 cooperates with each of $132_A$ and $132_B$ of the surgical fastener 130 to form two respective compressive spaces $140_1$, $140_2$ (FIG. 10). Sidewalls 156 and 158 are configured to support respective legs $132_A$, $132_B$. As noted, the legs of the surgical fasteners formed farther from the cut-line, or slot 122 provide a loop with a larger tissue compression zone $140_2$ and the legs of the surgical fasteners formed closer to the cut-line, or longitudinal slot 122 provide a loop with a smaller tissue compression zone $140_1$, see FIGS. 5A and 5B for example. Thus, because leg $132_B$ has a length "$L_2$" that is greater than leg $132_A$ and is supported by a sidewall 158 with a height "$H_2$" that is smaller than sidewall 156, a larger loop is formed when urged against a respective anvil portion. The resultant compression space or zone $140_2$ facilitates hemostasis. However, because blood flow is not completely restricted through tissue compression space $140_2$, unnecessary necrosis of the stapled tissue may be prevented and/or impeded. Conversely, because leg $132_A$ has a length "$L_1$" that is less than leg $132_B$ and is supported by a sidewall 136 with a height "$H_1$" that is larger than sidewall $132_B$, a smaller loop is formed when urged against a respective anvil portion. The resultant compression space or zone $140_1$ further facilitates hemostasis. Here, because blood flow is substantially restricted through tissue compression space $140_1$, this results in facilitating and effectuating hemostatsis.

The respective dimensions of sidewalls 156 and 158 and legs $132_A$, $132_B$, may be altered, which, in turn, may alter the respective dimensions of the compressive spaces $140_1$ and $140_2$ occupied by stapled tissue segments "$T_1$", "$T_2$" when the respective surgical fasteners $130_A$ are in their formed conditions. By altering the respective dimensions of sidewalls 156 and 158, and/or legs $132_A$, $132_B$, any desired level of hemostasis and blood flow in the stapled tissue segments "$T_1$", "$T_2$" may be effectuated. Other various attributes of the tissue (e.g., thickness or the presence of scar tissue) may increase or diminish the level of hemostasis and blood flow in the stapled tissue segments. In further embodiments, the fasteners may have a smaller compression space adjacent the lateral sides of the cartridge and a larger compression space adjacent the longitudinal slot 122. In other embodiments, the heights of the pushers, length of the legs, or both, differ to form a fastener with compressive spaces that differ in size.

FIG. 11 illustrates the surgical fasteners 130 including legs $132_A$ and $132_B$, and respective pushers 150 having sidewalls 156 and 158 loaded within the cartridge body 112 shown in FIGS. 1 and 4. The surgical fasteners 130 and respective pushers 150 are arranged to define a pair of rows 128 of fastener retention slots 126 formed in the top wall 120. The pair of rows 128 are each spaced laterally from the longitudinal slot 122, on opposite sides thereof, and include inner and outer ends $128_A$ and $128_B$, respectively, such that the surgical fasteners 130 will be deployed on opposite sides of the cut-line, or longitudinal slot 122 created in the tissue upon fastening. That is, the legs $132_A$ of the fasteners 130, which are driven by cam wedges 644 and are supported by sidewall 156, provide a greater compressive force as there is a shorter distance between the inner surface of the backspan and the curve of the formed legs, and in the illustrated embodiment are provided closer to the cut line, or longitudinal slot 122. The legs $132_B$ of fasteners 130, which are also driven by cam wedges 644 and are supported by sidewall 158, provide a lesser compressive force as there is a greater distance between the inner surface of the backspan and the curve of the formed legs, and in the illustrated embodiment are provided farther from the cut line, or slot 122. It should be appreciated, however, that the fasteners can be placed in rows that are configured differently than the foregoing. For example, two or more rows are on either side of the slot 122, with the outer rows having compressive spaces that differ after forming, or having standard fasteners and/or some combination thereof.

In further embodiments, the shape of the cartridge or anvil or both applies a compression force to the tissue that varies depending on the location with respect to the cartridge and anvil. In certain embodiments, the cartridge or anvil or both are configured to apply a compression force to the tissue that corresponds to the compressive space or area of the fastener at that location.

In certain embodiments, a staple having legs of approximately the same length are formed using pushers configured as pusher 150 so that one leg of the staple is crimped more than the other.

In one particular embodiment, the rows 128, are comprised solely of surgical fasteners 130 such that the flow of blood through the tissue immediately surrounding the cut-line, or slot 122 is substantially restricted by formed legs $132_A$ of surgical fasteners 130, whereas the flow of blood through the tissue surrounding areas away from the cut-line, or slot 122 is less restricted by formed legs $132_B$ of surgical fasteners 130. Accordingly, the flow of blood is minimized in the tissue immediately adjacent the cut-line, or longitudinal slot 122 and is increased gradually as the lateral distance from the cut-line is also increased. It should be appreciated that some of the fasteners in cartridge 100 can have different configurations, e.g., the diameters of the fasteners could be varied to accommodate tissue of different thicknesses and to control tissue compression by the fasteners. In addition, the formed configuration of the fasteners can be varied to vary the tissue compression applied by the fasteners. For example, the backspan of the fastener $130_A$ may be dimpled or crimped to decrease the compression space of the formed fastener.

From the foregoing and with reference to the various figure drawings, those skilled in the art will appreciate that certain modifications can also be made to the present disclosure without departing from the scope of the same. For example, the surgical fasteners described herein above may be formed from a variety of surgically acceptable materials including titanium, plastics, bio-absorbable materials, etc. Additionally, any of the aforementioned surgical fasteners may be treated, chemically or otherwise, prior to being loaded into cartridge 100.

It is also contemplated that the backspan 134 of the surgical fastener 130 may include one or more pockets (see FIG. 7C, for example) that are positioned to engage (i.e., receive or bend) the legs 132 during formation of the surgical fastener 130 and configured to redirect the legs 132 such that they are coiled toward the backspan 134, as discussed in commonly owned U.S. patent application Ser. No. 11/444,664, filed Jun. 1, 2006, the entire contents of which are incorporated by reference herein.

Figure 7A:
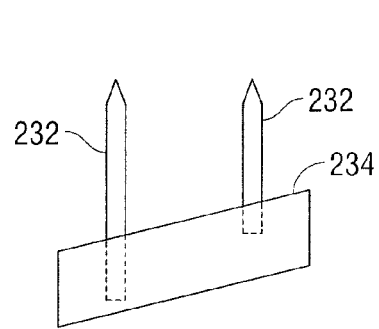
FIGS. 7A-7E illustrate alternate embodiments of surgical fasteners according to the present disclosure.
Figure 7B:
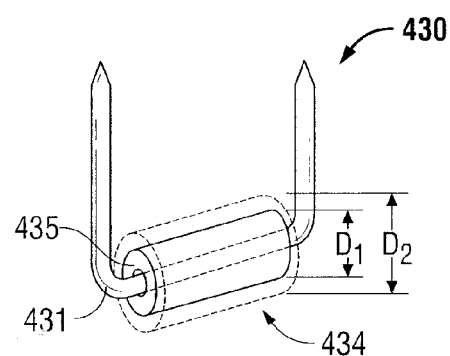
Figure 7C:
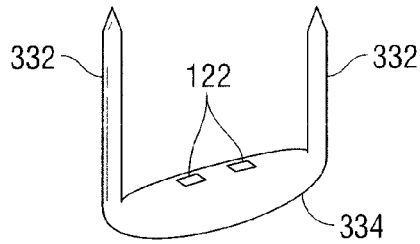
Figure 7D:
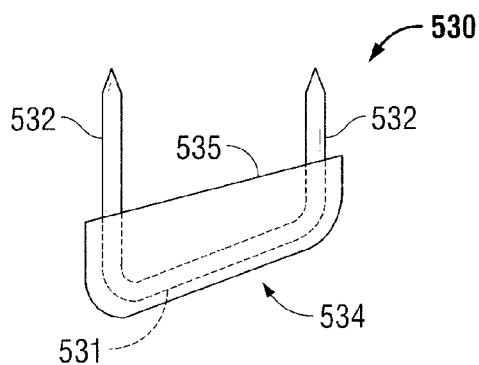
Figure 7E:
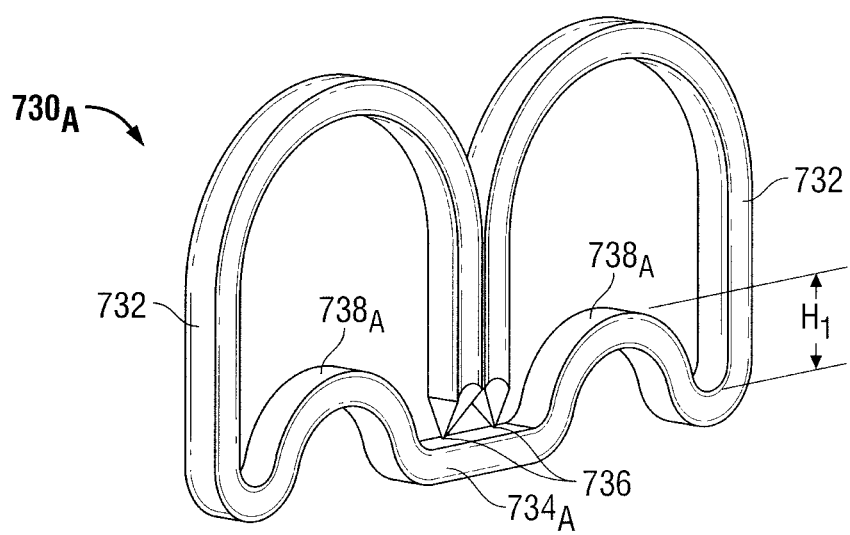

It is contemplated that in addition to varying the respective heights and lengths of the pusher 150 and surgical fastener 130, the thickness of the backspan 134 and the legs $132_A$ and $132_B$ may also be varied such that one leg of the surgical fastener 130 provides a greater compression force to stapled tissue occupied therein than the other leg of the surgical fastener 130. For example, in the embodiment of FIGS. 6 and 8, the backspan and legs are shown having a uniform diameter. It should be appreciated that the diameter of the legs and backspan, or portions thereof, can vary within the fastener. Examples of varying backspan sizes are shown in FIGS. 7A-7B. In the embodiment of FIG. 7A, the backspan is enlarged with respect to the legs and is an integral element 234 in which the fastener legs 232 are embedded. In FIG. 7C, the backspan is 334 is integral with the fastener legs 332. In the embodiments of FIGS. 7B and 7D, a separate backspan material is attached to the fastener 430, 530, respectively, with backspan 434 of FIG. 7B including a cylindrical collar 435 encircling the backspan portion 431 of the fastener 430 and the backspan 534 of fastener 530 of FIG. 7D encompassing the backspan portion 531 of the fastener and a portion of the fastener legs 532. In the embodiment of FIG. 7E, a surgical fastener $730_A$ is shown in its formed condition. The surgical fastener $730_A$ includes recesses, humps or mounds $738_A$ formed in the backspan $734_A$. Recesses extend inwardly from the backspan $734_a$ curving towards the penetrating ends 736 of the legs 732 and defining a recess, hump or mound of a first height "$H_1$". The backspan material of FIGS. 7B and 7D can be composed of any suitable material, by way of example, a resilient form, elastomer, or molder plastic can be used. Varying the thickness or height of these backspans or backspan materials can vary the compression force of the formed staple by varying the distance between the curved legs and inner portion of the backspan. This variation can be provided in addition to the varying gap distances of the cam wedges to accommodate varying tissue thicknesses. FIG. 7B illustrates this varying backspan by showing in phantom a collar of larger diameter (D2 compared to D1) to decrease the compression area. Other backspan shapes and attachments to achieve the various compression forces are also contemplated.

The surgical fastener applying apparatus according to certain embodiments of the present disclosure includes a plurality of cam bars for interacting with the pushers to deploy the surgical fasteners. For example, the apparatus disclosed in U.S. Pat. No. 5,318,221, the disclosure of which is hereby incorporated by reference herein, in its entirety, has a cam bar adapter that holds a plurality of cam bars and a knife. A slot is advanced through operation of the handle of the apparatus, which drives the cam bars and knife forward. A clamp tube that surrounds the proximal end of the anvil is advanced to clamp the anvil and cartridge together. In another example, the apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the slot that supports the cartridge as the drive beam travels distally, to deploy the staples and clamp the anvil and cartridge together. The surgical fastener applying apparatus shown in U.S. Pat. No. 7,070,083 employs a pusher bar incorporating a plurality of pushers that are advanced substantially simultaneously to deploy the fasteners against an anvil. One or more of the pushers may incorporate a deflectable portion, in certain embodiments of the present disclosure.

Figure 12:
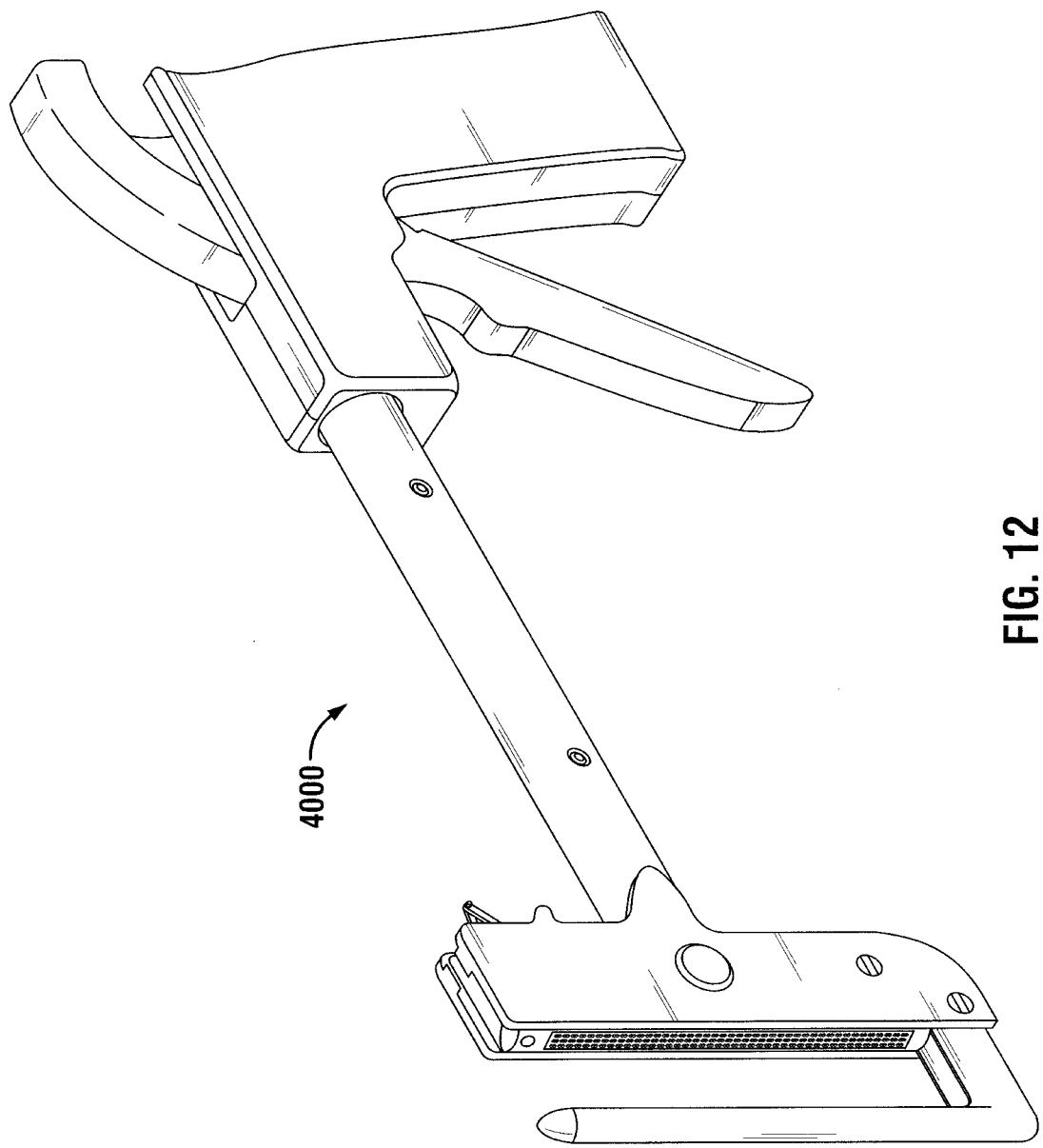
FIG. 12 illustrates another type of surgical fastener device that may employ an alternate embodiment of surgical fastener cartridge in accordance with the present disclosure.

The surgical fastening cartridge 100 may also be employed with a surgical fastener applying apparatus 4000 (FIG. 12). Apparatus 4000 has a drive bar that advances distally that is typically used to simultaneously deploy a plurality of surgical fasteners (surgical fasteners 130 for example) into a target section of tissue (not explicitly shown). Here, a scalpel or other such cutting element may be used to remove the target section of tissue. Further details regarding the use and function of surgical fastener applying apparatus 4000 may be obtained through reference to U.S. Pat. No. 7,070,083 the entire contents of which having been previously incorporated by reference herein. In an alternate embodiment, the apparatus 4000 could include a cutting element as in the other cartridges disclosed herein.

Although the illustrative embodiments of the present disclosure have been described herein with reference to the accompanying drawings, the above description, disclosure, and figures should not be construed as limiting, but merely as exemplary of various embodiments.

What is claimed is:

1. A non-reloadable surgical fastener cartridge comprising:
a cartridge body including a tissue contacting surface, the tissue contacting surface including a plurality of fastener retention slots and a knife slot;
a plurality of surgical fasteners disposed in the plurality of fastener retention slots, each surgical fastener having a first end that is closer to the knife slot than a second end;
a plurality of pushers operably associated with the plurality of surgical fasteners, each pusher configured for ejecting an associated surgical fastener towards a depression in an anvil, each of the pushers has a corresponding surgical fastener and first and second sidewalls, the first sidewall having a height larger than a height of the second sidewall such that, upon formation, the first end of the corresponding surgical fastener is smaller in height than the second end of the corresponding surgical fastener; and
an actuation mechanism operably associated with the plurality of pushers.

2. A non-reloadable surgical fastener cartridge according to claim 1, wherein the corresponding surgical fasteners has a first leg at the first end and a second leg at the second end, the first leg including a length that is shorter than a length of the second leg.

3. A non-reloadable surgical fastener cartridge according to claim 1, wherein each of the plurality of fastener retention slots are angled forming inner and outer ends with respect to the knife slot.

4. A non-reloadable surgical fastener cartridge according to claim 1, wherein each of the formed surgical fasteners includes a first loop and a second loop.

5. A non-reloadable surgical fastener cartridge according to claim 1, wherein the first and second leg of each of the surgical fastener are connected by a backspan that defines an angle with respect to the tissue contacting surface.

6. A non-reloadable surgical fastener cartridge according to claim 1, wherein at least one of the pushers has a top surface that is sloped.

7. A non-reloadable surgical fastener cartridge according to claim 6, wherein the backspan follows substantially the same contour as the top surface the pusher.

* * * * *